(12) United States Patent
Bae et al.

(10) Patent No.: US 12,257,034 B2
(45) Date of Patent: Mar. 25, 2025

(54) APPARATUS AND METHOD FOR ESTIMATING BIO-INFORMATION

(71) Applicants: SAMSUNG ELECTRONICS CO., LTD., Suwon-si (KR); IUCF-HYU (INDUSTRY-UNIVERSITY COOPERATION FOUNDATION HANYANG UNIVERSITY), Seoul (KR)

(72) Inventors: Sang Kon Bae, Seongnam-si (KR); Joon-Hyuk Chang, Seoul (KR); Jin Woo Choi, Suwon-si (KR); Youn Ho Kim, Hwaseong-si (KR); Jehyun Kyung, Seoul (KR); Joon-Young Yang, Seoul (KR); Inmo Yeon, Seoul (KR); Jeong-Hwan Choi, Seoul (KR)

(73) Assignees: SAMSUNG ELECTRONICS CO., LTD., Suwon-si (KR); IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 924 days.

(21) Appl. No.: 17/369,199

(22) Filed: Jul. 7, 2021

(65) Prior Publication Data

US 2022/0287571 A1    Sep. 15, 2022

(30) Foreign Application Priority Data

Mar. 10, 2021 (KR) ......... 10-2021-0031320

(51) Int. Cl.
*A61B 5/0205* (2006.01)
*A61B 5/00* (2006.01)
(Continued)

(52) U.S. Cl.
CPC ........ *A61B 5/0205* (2013.01); *A61B 5/02007* (2013.01); *A61B 5/02225* (2013.01);
(Continued)

(58) Field of Classification Search
CPC . A61B 5/0205; A61B 5/02225; A61B 5/6843; A61B 5/7239; A61B 5/7267; G06N 3/045; G06N 3/0464
See application file for complete search history.

(56) References Cited

U.S. PATENT DOCUMENTS 11,213,216 B2    1/2022  Choi et al.
11,276,127 B1 *  3/2022  Stevens ................. G06Q 50/01
(Continued)

FOREIGN PATENT DOCUMENTS

CN    111248883 A    6/2020
EP    3 649 928 A2    5/2020
(Continued)

OTHER PUBLICATIONS

M. Schwob, et al. Robust Multimodal Heartbeat Detection Using Hybrid Neural Networks (Apr. 27, 2020), IEEE Access, 82201-12 (Year: 2020).*

(Continued)

*Primary Examiner* — David Yi
*Assistant Examiner* — Evan Lehrer
(74) *Attorney, Agent, or Firm* — Sughrue Mion, PLLC

(57) ABSTRACT

An apparatus for estimating bio-information is disclosed. The apparatus may include: a pulse wave sensor configured to measure a pulse wave signal from an object; a force sensor configured to obtain a force signal by measuring an external force exerted onto the force sensor; and a processor configured to obtain a first input value, a second input value, and a third input value based on the pulse wave signal and the force signal, to extract a feature vector by inputting the (Continued)

first input value, the second input value, and the third input value into a first neural network model, and to obtain the bio-information by inputting the feature vector into a second neural network model.

25 Claims, 15 Drawing Sheets

(51) Int. Cl.
*A61B 5/02* (2006.01)
*A61B 5/022* (2006.01)
*G06N 3/045* (2023.01)
*G06N 3/0464* (2023.01)

(52) U.S. Cl.
CPC .............. *A61B 5/442* (2013.01); *A61B 5/681* (2013.01); *A61B 5/6843* (2013.01); *A61B 5/6898* (2013.01); *A61B 5/7239* (2013.01); *A61B 5/7267* (2013.01); *G06N 3/045* (2023.01); *G06N 3/0464* (2023.01); *A61B 2562/0247* (2013.01)

(56) References Cited

U.S. PATENT DOCUMENTS

| | | | |
|---|---|---|---|
| 2018/0078139 | A1 | 3/2018 | Sanders et al. |
| 2018/0107798 | A1 | 4/2018 | Hu |
| 2018/0140228 | A1 | 5/2018 | Olivier |
| 2018/0214088 | A1 | 8/2018 | Newberry |
| 2018/0235493 | A1 | 8/2018 | Zhang |
| 2020/0015690 | A1 | 1/2020 | Choi et al. |
| 2020/0015755 | A1 | 1/2020 | Zhao et al. |
| 2020/0146568 | A1 | 5/2020 | Park et al. |
| 2020/0160521 | A1* | 5/2020 | Wang .................... G06V 40/193 |
| 2020/0201971 | A1 | 6/2020 | Wei et al. |
| 2020/0297220 | A1* | 9/2020 | Lu ............................ G06F 21/31 |
| 2020/0323440 | A1* | 10/2020 | Vule ....................... A61B 5/681 |
| 2021/0015431 | A1* | 1/2021 | Kang ...................... G06N 3/045 |
| 2021/0030278 | A1 | 2/2021 | Choi et al. |
| 2021/0125732 | A1* | 4/2021 | Patel ......................... G06N 5/01 |
| 2021/0251567 | A1* | 8/2021 | Wu ........................ A61B 5/7239 |
| 2022/0019870 | A1* | 1/2022 | Gu .......................... G06N 3/045 |
| 2022/0087556 | A1 | 3/2022 | Choi et al. |
| 2022/0122692 | A1* | 4/2022 | Feala ....................... G16B 15/20 |
| 2022/0130520 | A1* | 4/2022 | Xia ......................... G16H 30/40 |
| 2022/0169381 | A1* | 6/2022 | Alrasheed ............. B64C 39/024 |
| 2022/0172074 | A1* | 6/2022 | Luo ........................ G06N 3/045 |
| 2022/0207331 | A1* | 6/2022 | Andoche .............. G06V 10/764 |
| 2023/0036463 | A1* | 2/2023 | Yang ..................... G06T 7/0012 |

FOREIGN PATENT DOCUMENTS

| | | |
|---|---|---|
| JP | 2018-067303 A | 4/2018 |
| KR | 10-1857624 B1 | 5/2018 |
| KR | 10-2019-0056858 A | 5/2019 |
| KR | 10-2042700 B1 | 11/2019 |
| KR | 10-2020-0004667 A | 1/2020 |
| KR | 1020200007503 A | 1/2020 |
| KR | 1020210014305 A | 2/2021 |

OTHER PUBLICATIONS

M. Arsalan, et al. Aiding the Diagnosis of Diabetic and Hyptensive Retinopathy Using Artifical Intelligence-Based Semtanic Segmentation (Sep. 11, 2019), Journal of Clinical Medicine, p. 7. (Year: 2019).*
R. Punia, et al. Computer Vision and Radiology for COVID-19 Detection (Jun. 7, 2020), International Conference for Emerging Technology, p. 3. (Year: 2020).*
Raghuram Nandepu, Understanding and Implementation of Residual Networks ResNets (Oct. 30, 2019), Medium retrieved at https://medium.com/analytics-vidhya/understanding-and-implementation-of-residual-networks-resnets-b80f9a507b9c (date accessed Jun. 24, 2024) (Year: 2019).*
Smith, Steven (2003), Digital signal processing: a practical guide for engineers and scientists. Newnes, p. 274 (Year: 2003).*
Communication dated Oct. 31, 2022 issued by the Korean Intellectual Property Office in KR Patent Application No. 10-2021-0031320.
Communication dated Feb. 23, 2022, issued by the European Patent Office in counterpart European Application No. 21196633.8.
Schlesinger et al., "Blood Pressure Estimation From PPG Signals Using Convolutional Neural Networks and Siamese Network," IEEE, ICASSP 2020, pp. 1135-1139.
Tjahjadi et al., "Noninvasive Classification of Blood Pressure Based on Photoplethysmography Signals Using Bidirectional Long Short-Term Memory and Time-Frequency Analysis," IEEE Access, IEEE Engineering in Medicine and Biology Society Section, vol. 8, 2020, pp. 20735-20748.
Baek et al., "End-to-End Blood Pressure Prediction via Fully Convolutional Networks," IEEE Access, Special Section on Data-Enabled Intelligence for Digital Health, vol. 7, 2019, pp. 185458-185468.
Shimazaki et al., "Cuffless Blood Pressure Estimation from only the Waveform of Photoplethysmography using CNN," 2019 41st Annual International Conference of the IEEE Engineering in Medicine and Biology Society (EMBC), 2019, total 3 pages.
Eloff et al., "Unsupervised acoustic unit discovery for speech synthesis using discrete latent-variable neural networks," arXiv:1904.07556v2 [cs.CL], Jun. 28, 2019, Total 5 pages.

* cited by examiner

APPARATUS AND METHOD FOR ESTIMATING BIO-INFORMATION

CROSS-REFERENCE TO RELATED APPLICATION(S)

This application claims priority from Korean Patent Application No. 10-2021-0031320, filed on Mar. 10, 2021, in the Korean Intellectual Property Office, the disclosure of which is incorporated herein by reference in its entirety.

BACKGROUND

1. Field

The following description relates to an apparatus and method for non-invasively estimating bio-information, and more particularly to technology for estimating bio-information by using an estimation model based on deep learning.

2. Description of the Related Art

Generally, methods of non-invasively measuring blood pressure without causing pain to a human body include a method to measure blood pressure by measuring a cuff-based pressure and a method to estimate blood pressure by measuring pulse waves without the use of a cuff. A Korotkoff-sound method is one of cuff-based blood pressure measurement methods, in which a pressure in a cuff wound around an upper arm is increased and blood pressure is measured by listening to the sound generated in the blood vessel through a stethoscope while decreasing the pressure. Another cuff-based blood pressure measurement method is an oscillometric method using an automated machine, in which a cuff is wound around an upper arm, a pressure in the cuff is increased, a pressure in the cuff is continuously measured while the cuff pressure is gradually decreased, and blood pressure is measured based on a point where a change in a pressure signal is large. Cuffless blood pressure measurement methods generally include a method of estimating blood pressure by calculating a Pulse Transit Time (PTT), and a Pulse Wave Analysis (PWA) method of estimating blood pressure by analyzing a pulse wave shape.

SUMMARY

According to an aspect of an example embodiment, there is provided an apparatus for estimating bio-information, the apparatus including: a pulse wave sensor configured to measure a pulse wave signal from an object; a force sensor configured to obtain a force signal by measuring an external force exerted onto the force sensor; and a processor configured to obtain a first input value, a second input value, and a third input value based on the pulse wave signal and the force signal, to extract a feature vector by inputting the obtained first input value, second input value, and third input value into a first neural network model, and to obtain bio-information by inputting the extracted feature vector into a second neural network model.

The first neural network model and the second neural network model may be based on at least one of a Deep Neural Network, a Convolution Neural Network (CNN), and a Recurrent Neural Network (RNN).

The first neural network model may include three neural networks, which are arranged in parallel, and into which the first input value, the second input value, and the third input value are input respectively, and a fully connected layer outputting the feature vector by using outputs of the three neural networks as inputs.

Each of the three neural networks may include a first block and a second block. The first block may include a first convolution layer, a first batch normalization layer, a first activation function layer, and a first pooling layer. The second block may include a second convolution layer, a second batch normalization layer, a second activation function layer, a third convolution layer, a third batch normalization layer, a skip connection path, and a third activation function.

The second neural network model may include a first fully connected layer using the feature vector as an input, and a second fully connected layer outputting the bio-information by using an output of the first fully connected layer as an input.

The second neural network model may further include a third fully connected layer using, as an input, an additional feature extracted based on at least one of user characteristic information including at least one of age, gender, stature, and weight, wherein an output of the third fully connected layer may be input into the second fully connected layer.

The processor may generate a first order differential signal and a second order differential signal from the pulse wave signal, and may obtain at least one of the pulse wave signal, the first order differential signal, and the second order differential signal as the first input value.

By using the force signal, the processor may generate at least one envelope of an envelope of the pulse wave signal, an envelope of the first order differential signal, and an envelope of the second order differential signal, and may obtain the at least one envelope as the second input value.

The processor may obtain the force signal as the third input value.

The processor may be further configured to obtain, as the third input value, the force signal by measuring the force during a predetermined time period, starting from a reference point in time that corresponds to a maximum amplitude point in the envelope of the pulse wave signal.

The processor may preprocess the pulse wave signal and the force signal by using at least one of a band pass filter and a low pass filter.

The processor may obtain an additional feature based on at least one of user characteristic information, the pulse wave signal, and the force signal, and may obtain the bio-information by inputting the feature vector and the obtained additional feature into the second neural network model.

The bio-information may include one or more of blood pressure, vascular age, arterial stiffness, aortic pressure waveform, vascular compliance, stress index, fatigue level, skin age, skin elasticity.

The first neural network model and the second neural network model may be jointly trained, by using a plurality of reference pulse wave signals and a plurality of reference force signals corresponding to the plurality of reference pulse wave signals, as training data.

The first neural network model may be trained by inputting to the first neural network model, a first reference input value, a second reference input value, and a third reference input value that are obtained based on the plurality of reference pulse wave signals and the plurality of reference force signals. The second neural network model be trained by inputting, to the second neural network model, a reference feature vector that is output from the first neural network model.

According to an aspect of another example embodiment, there is provided a method of estimating bio-information by an electronic device, the method including: measuring a pulse wave signal from an object, and measuring a force signal exerted on the object; obtaining a force signal by measuring force exerted onto the electronic device by the object; obtaining a second input value based on the pulse wave signal and the force signal; obtaining a third input value based on the force signal; extracting a feature vector by inputting the first input value, the second input value, and the third input value into a first neural network model; and obtaining the bio-information by inputting the feature vector into a second neural network model.

The first neural network model may include three neural networks, which are arranged in parallel and into which the first input value, the second input value, and the third input value are input respectively, and a fully connected layer outputting the feature vector by using outputs of the three neural networks as inputs.

Each of the three neural networks may include a first block and a second block. The first block may include a first convolution layer, a first batch normalization layer, a first activation function layer, and a first pooling layer. The second block may include a second convolution layer, a second batch normalization layer, a second activation function layer, a third convolution layer, a third batch normalization layer, a skip connection layer, and a third activation function layer.

The second neural network model may include a first fully connected layer using the feature vector as an input, and a second fully connected layer outputting bio-information by using an output of the first fully connected layer as an input.

The second neural network model may further include a third fully connected layer using, as an input, an additional feature extracted based on at least one of user characteristic information, the pulse wave signal, and the force signal, wherein an output of the third fully connected layer may be input into the second fully connected layer.

The obtaining of the first input value may include generating a first order differential signal and a second order differential signal from the pulse wave signal, and obtaining at least one of the pulse wave signal, the first order differential signal, and the second order differential signal as the first input value.

The obtaining of the second input value may include, by using the force signal, generating at least one envelope of an envelope of the pulse wave signal, an envelope of the first order differential signal, and an envelope of the second order differential signal, and obtaining the generated at least one envelope as the second input value.

The obtaining of the third input value may include obtaining the force signal as the third input value.

The obtaining of the third input value may include obtaining, as the third input value, the force signal by measuring the force during a predetermined time period, starting from a reference point in time that corresponds to a maximum amplitude point in the envelope of the pulse wave signal.

In addition, the method of estimating bio-information may further include obtaining an additional feature based on at least one of user characteristic information, the pulse wave signal, and the force signal, wherein the obtaining of the bio-information may include inputting the feature vector and the obtained additional feature into the second neural network model to obtain the bio-information.

According to an aspect of an example embodiment, there is provided an electronic device including a main body, the apparatus for estimating the bio-information which is disposed in the main body, and display configured to output a processing result of the apparatus.

The electronic device may correspond to a wristwatch wearable device, an ear-wearable device, or a mobile device.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
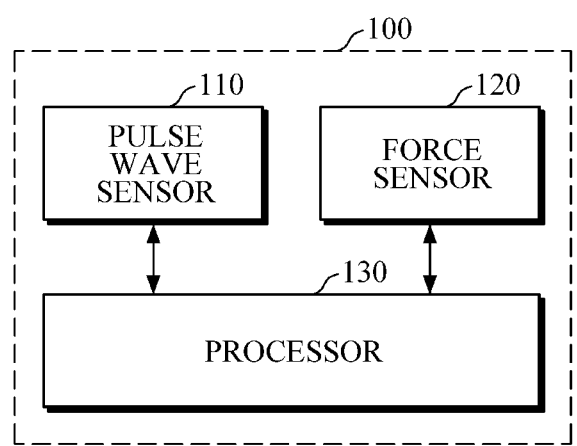
FIG. 1 is a block diagram illustrating an apparatus for estimating bio-information according to an embodiment of the present disclosure.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. It will be further understood that when an element is referred to as "comprising" another element, the element is intended not to exclude one or more other elements, but to further include one or more other elements, unless explicitly described to the contrary. In the following description, terms such as "unit" and "module" indicate a unit for processing at least one function or operation and they may be implemented by using hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of an apparatus and method for estimating bio-information will be described in detail with reference to the accompanying drawings.

FIG. 1 is a block diagram illustrating an apparatus for estimating bio-information according to an embodiment of the present disclosure.

Referring to FIG. 1, the apparatus 100 for estimating bio-information includes a pulse wave sensor 110, a force sensor 120, and a processor 130.

The pulse wave sensor 110 may measure a pulse wave signal, such as for example, a photoplethysmography (PPG) signal, while the pulse wave sensor 110 maintains contact with an object. The object may be a body part, which may come into contact with the pulse wave sensor 110, and at which pulse waves may be easily measured. For example, the object may be a finger where blood vessels are densely distributed, but the object is not limited thereto and may be an area on a wrist that is adjacent to a radial artery, and an upper portion of the wrist where veins or capillaries are located, or a peripheral part of a body, such as, toes, and the like.

The pulse wave sensor 110 may include one or more light sources configured to emit light onto the object, and one or more detectors disposed at positions spaced apart from the light sources by a predetermined distance, and configured to detect light scattered or reflected from the object. The one or more light sources may emit light of different wavelengths. For example, the light sources may emit light of an infrared wavelength, a green wavelength, a blue wavelength, a red wavelength, a white wavelength, and the like. The light sources may include any one or any combination of a light emitting diode (LED), a laser diode (LD), a phosphor, etc., but are not limited thereto. Further, the detectors may include any one or any combination of a photodiode, a photodiode array, a complementary metal-oxide semiconductor (CMOS) image sensor, a charge-coupled device (CCD) image sensor, and the like.

Further, the force sensor 120 may measure a force signal when the object is in contact with the pulse wave sensor 110 and gradually increases or decreases a pressing force against the force sensor 120 to induce a change in pulse wave amplitude. The force sensor 120 may be formed as a single force sensor including a strain gauge and the like, or may be formed as an array of force sensors. However, the implementation of the force sensor 120 is not limited thereto, and instead of the force sensor 120, a pressure sensor, an air bladder type pressure sensor, a pressure sensor in combination with a force sensor and an area sensor, and the like may be provided.

The processor 130 may estimate bio-information based on the pulse wave signal, measured by the pulse wave sensor 110, and the contact force measured by the force sensor 120. The bio-information may include information of blood pressure, vascular age, arterial stiffness, aortic pressure waveform, vascular compliance, stress index, fatigue level, skin age, and/or skin elasticity, but is not limited thereto. For convenience of explanation, the following description will be given using blood pressure as an example if necessary, but the present disclosure is not limited to blood pressure.

Figure 2A:
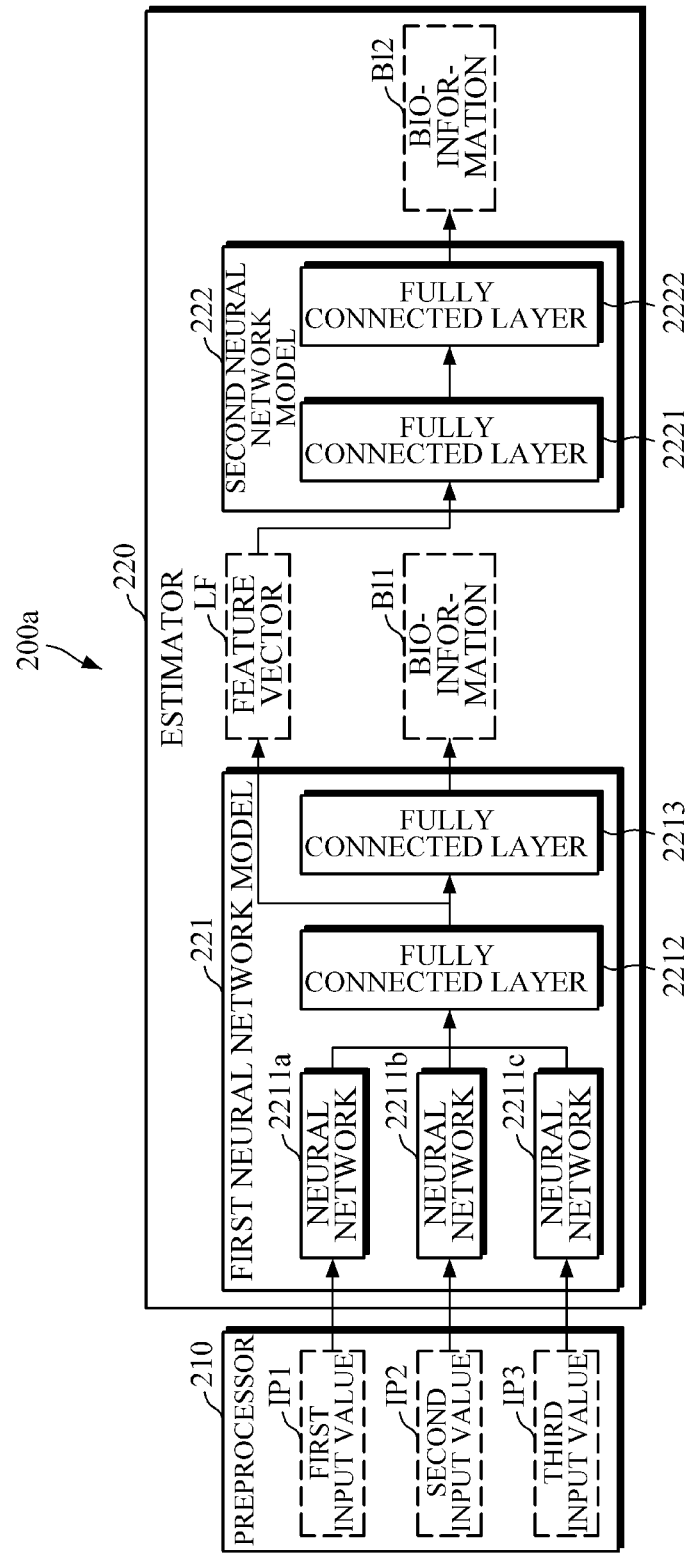
FIGS. 2A to 2C are diagrams explaining examples of a configuration of a processor according to the embodiment of FIG. 1.
Figure 2B:
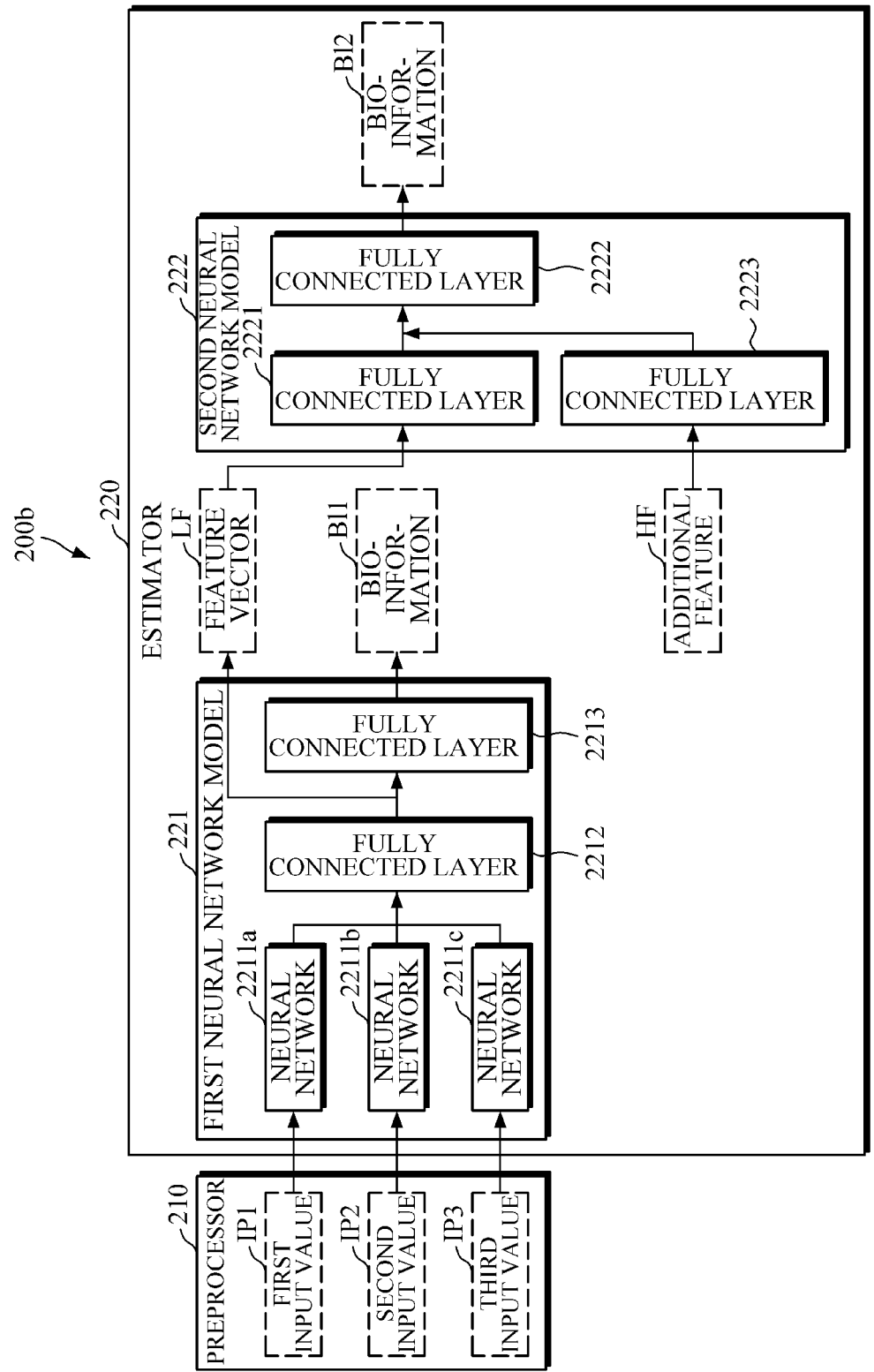
Figure 2C:
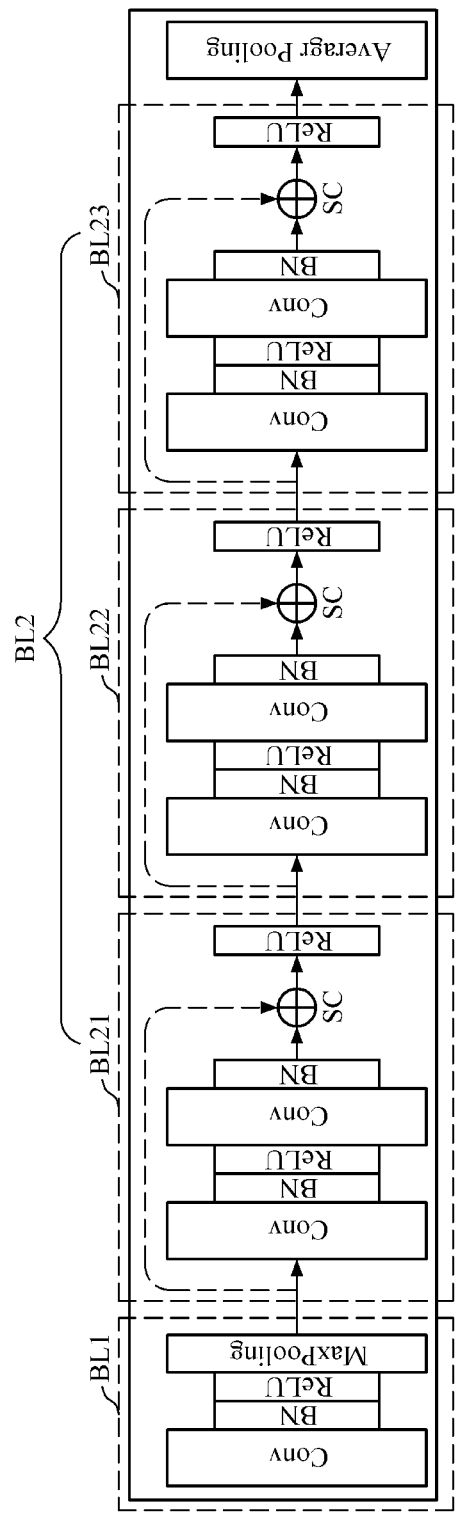
Figure 2D:
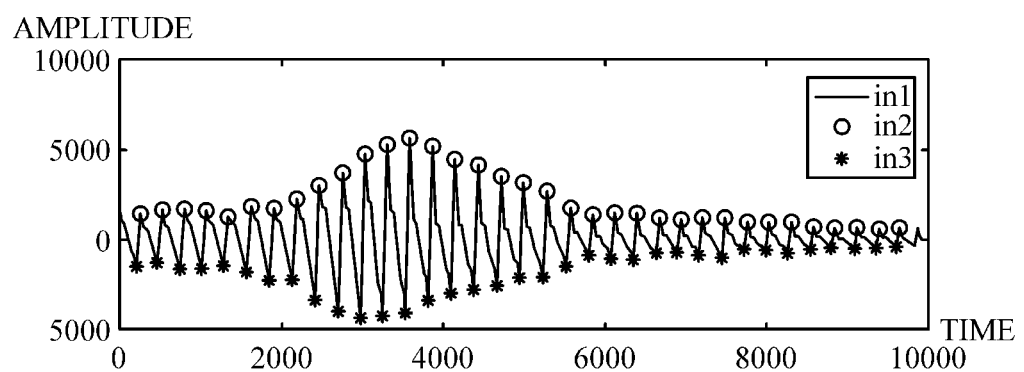
FIG. 2D is a diagram illustrating an example of a pulse wave signal acquired by a pulse wave sensor.
Figure 2E:
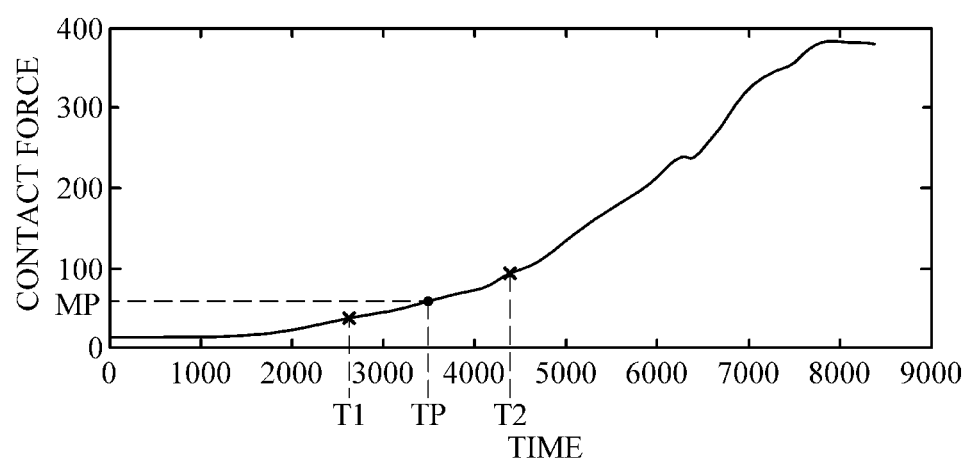
FIG. 2E is a diagram illustrating an example of a force signal acquired by a force sensor.
Figure 2F:
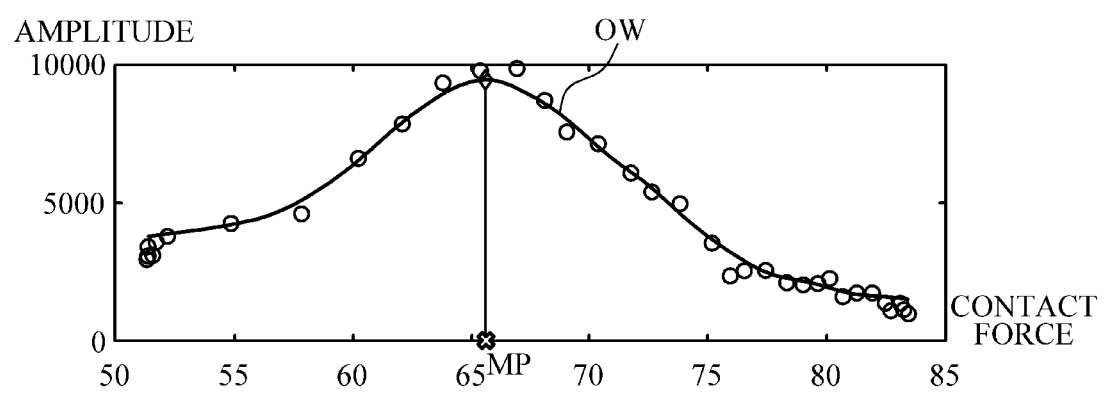
FIG. 2F is a diagram illustrating an example of an oscillometric envelope obtained by using a pulse wave signal and a force signal.

FIGS. 2A to 2C are diagrams explaining examples of a configuration of a processor according to the embodiment of FIG. 1. FIG. 2D is a diagram illustrating an example of a pulse wave signal acquired by a pulse wave sensor. FIG. 2E is a diagram illustrating an example of a force signal acquired by a force sensor. FIG. 2F is a diagram illustrating an example of an oscillometric envelope obtained by using a pulse wave signal and a force signal.

Referring to FIGS. 2A and 2B, processors 200a and 200b according to the embodiments may include a preprocessor 210 and an estimator 220.

The preprocessor 210 may preprocess a pulse wave signal and/or a force signal, received from the pulse wave sensor 110 and/or the force sensor 120, by using a band pass filter and/or a low pass filter, and the like. For example, the preprocessor 210 may perform band pass filtering on the pulse wave signal, with a cut-off frequency of 1 Hz to 10 Hz.

In addition, by using the pulse wave signal and/or the force signal, the preprocessor 210 may obtain input values to be input to the estimator 220.

For example, the preprocessor 210 may obtain a first input value by using the pulse wave signal. For example, the preprocessor 210 may convert the pulse wave signal to a first order differential signal and/or a second order differential signal by performing first order differentiation and/or second order differentiation on the pulse wave signal. The preprocessor 210 may obtain the pulse wave signal, the first order differential signal and/or the second order differential signal as the first input values. In particular, the preprocessor 210 may extract a portion of the pulse wave signal, the first order differential signal and/or the second order differential signal, within a predetermined time period, as the first input values. The predetermined time period may be pre-defined based on a time point corresponding to a maximum amplitude point of the pulse wave signal. For example, when the maximum amplitude point appears at time $T_{max}$, the predetermined time period may be set to a range from time $T_1$ to time $T_2$, wherein the $T_{max}$ is between time $T_1$ and time $T_2$.

Further, the preprocessor 210 may obtain an envelope of the pulse wave signal, an envelope of the first order differential signal and/or an envelope of the second order differential signal by using the pulse wave signal, the first order differential signal and/or the second order differential signal, and the force signal. The preprocessor 210 may obtain the envelope of the pulse wave signal, the envelope of the first order differential signal and/or the envelope of the second order differential signal as second input values. The preprocessor 210 may extract a portion of the envelope of the pulse wave signal, the envelope of the first order differential signal and/or the envelope of the second order differential signal, within a predetermined time period, as the second input value. In this case, the predetermined time period may be pre-defined based on a time point corresponding to a maximum amplitude point of the pulse wave signal.

Referring to FIGS. 2D to 2F, an example of obtaining an envelope will be described below. The preprocessor 210 may extract, e.g., a peak-to-peak point of the pulse wave signal waveform by subtracting a negative (−) amplitude value in3 from a positive (+) amplitude value in2 of a waveform envelope in1 at each measurement time of the pulse wave signal. Further, the preprocessor 210 may obtain an envelope (OW) of the pulse wave signal by plotting the peak-to-peak amplitude at each measurement time against a contact pressure value at a corresponding time point and by performing, for example, polynomial curve fitting. Likewise, by using the first order differential signal and the force signal and/or the second order differential signal and the force signal, the preprocessor 210 may obtain an envelope of the first order differential signal and/or an envelope of the second order differential signal.

In addition, the preprocessor 210 may obtain a third input value by using the force signal. For example, the preprocessor 210 may determine a force signal over the entire interval to be the third input value. Alternatively, as illustrated in FIG. 2E, the preprocessor 210 may determine, as the third input value, a force signal over predetermined time intervals T1 and T2 from a reference point TP, for example, a time interval of 5 seconds in total, with preceding and subsequent time intervals of 2.5 seconds each. In this case, the reference point TP may be a time point corresponding to a maximum amplitude point MP in an envelope of the pulse wave signal illustrated in FIG. 2F. However, the interval is not limited thereto, and an interval of force applied by the object may be pre-defined, and the interval of force may be defined differently for each user.

Referring back to FIGS. 2A and 2B, the estimator 220 may include a first neural network model 221 and a second neural network model 222. The first neural network model 221 and the second neural network model 222 may be implemented by Deep Neural Network (DNN), Convolution Neural Network (CNN), Recurrent Neural Network (RNN), or the like. In particular, the first neural network model 221 may be a neural network model trained to output a feature vector associated with blood pressure and/or an estimated blood pressure value by using the input values, obtained by the preprocessor 210, as inputs; and the second neural network model 222 may be a neural network model trained to output an estimated blood pressure value by using the feature vector of the first neural network model and/or other additional features as inputs.

The first neural network model 221 may include three neural networks 2211a, 2211b, and 2211c and one or more fully connected layers 2212 and 2213. The respective neural networks 2211a, 2211b, and 2211c are arranged in parallel as illustrated herein for parallel processing, and a first input value IP1, a second input value IP2, and a third input value IP3 obtained by the preprocessor 210 may be input into the neural network models 2211a, 2211b, and 2211c, respectively.

Referring to FIG. 2C, the respective neural network models 2211a, 2211b, and 2211c may be residual neural network-based neural networks. As illustrated in FIG. 2C, the respective neural network models 2211a, 2211b, and 2211c may be composed of a first block BL1, a second block BL2, followed by an average pooling. The first block BL1 may include a convolution layer Conv, a batch normalization layer BN, an activation function layer ReLU, and a max pooling layer MaxPooling. The second block BL2 may include one or more sub-blocks BL21, BL22, and BL23. Each of the sub-blocks BL21, BL22, and BL23 may include a convolution layer Conv, a batch normalization layer BN, an activation function layer ReLU, a convolution layer Conv, a batch normalization layer BN, a skip connection (or a skip connection path) SC, and an activation function layer ReLU. In this case, the sub-blocks may be three in number, but the number is not limited thereto.

The convolutional layer Conv may convolute input features to extract high-level features (e.g., a maximum amplitude value). The batch normalization layer BN may normalize the high-level features, and the activation function layer ReLU may apply an activation function, for example, an ReLU function to the normalized high-level features. The max pooling layer MaxPooling may reduce the spatial size of the convolved feature by returning a maximum value from each data section covered by a filter. The skip connection SC may form a direct path between the output nodes of the preceding block and the input nodes of the activation function layer ReLU of the current block, so that the output of the max pooling layer MaxPooling in block BL1 is directly fed to the activation function layer ReLU in block BL2.

Referring back to FIGS. 2A and 2B, the first fully connected layer 2212 may be connected to the respective neural networks 2211a, 2211b, and 2211c, to equalize outputs of the respective neural networks 2211a, 2211b, and 2211c, and may convert the outputs into feature vectors LF associated with blood pressure. The second fully connected layer 2213 may output a first blood pressure value BI1 by using the feature vector, output from the first fully connected layer 2212, as an input. In addition, a Sigmoid Function may be further included after the first fully connected layer 2212.

Referring to FIG. 2A, the second neural network model 222 may include one or more fully connected layers 2221 and 2222. The feature vector LF associated with blood pressure, which is output from the first neural network model 221, may be input into the first fully connected layer 2221 of the second neural network model 222, and an output of the first fully connected layer 2221 may be input into the second fully connected layer 2222 to be converted into the second blood pressure value BI2. In this case, ReLu function and/or MaxOut function may be further included after the first fully connected layer 2221.

Referring to FIG. 2B, the second neural network model 222 may further include a third fully connected layer 2223. The third fully connected layer 2223 may use an additional feature HF associated with blood pressure, which is obtained by various other methods, as an input value. For example, the additional feature HF may include user characteristic information, such as age, gender, stature, and weight of a user, and the user characteristic information may be input from a user. Further, the additional feature HF may include additional information extracted by the preprocessor 210 from the pulse wave signal, the first order differential signal, the second order differential signal, and/or the force signal. Examples of the additional feature may include any one or any combination of amplitude/time values at a maximum amplitude point of each of the pulse wave signal, the first order differential signal, the second order differential signal, and/or the force signal, amplitude/time values at a local minimum point/local maximum point of each of the pulse wave signal, the first order differential signal, the second order differential signal, and/or the force signal, amplitude/time values at an inflection point of each of the pulse wave signal, the first order differential signal, the second order differential signal, and/or the force signal, or a total/partial area of each signal waveform of the pulse wave signal, the first order differential signal, the second order differential signal, and/or the force signal, a contact force value corresponding to a maximum amplitude point of each of the pulse wave signal, the first order differential signal, the second order differential signal, and/or the force signal, a contact force value having a predetermined ratio to the contact force value at the maximum amplitude point of each of the pulse wave signal, the first order differential signal, the second order differential signal, and/or the force signal.

The first neural network model 221 and the second neural network model 222 may be jointly trained in the same training cycle.

Generally, as the depth of a neural network layer increases, the problem of gradient vanishing occurs when the neural network is trained. In example embodiments of the present disclosure, however, a neural network model may be built with deep layers by using a residual neural network with skip connection, and the neural network model may be trained to estimate blood pressure through a complicated computation process by using the pulse wave signal, the force signal, and the like. In addition, by inputting in parallel various input values, obtained using the pulse wave signal and/or the force signal, into the neural networks 2221a, 2221b, and 2221c of the first neural network model 221, individual characteristics between blood pressure and the various input values may be considered, thereby improving accuracy in estimating blood pressure.

The estimator 220 may output the second blood pressure value BI2, that is output from the second neural network model 222, as a final estimated blood pressure value. Alternatively, the estimator 220 may linearly or non-linearly combine the first blood pressure value BI1 and the second blood pressure value BI2, and may output a resultant value as a final estimated blood pressure value.

Figure 3:
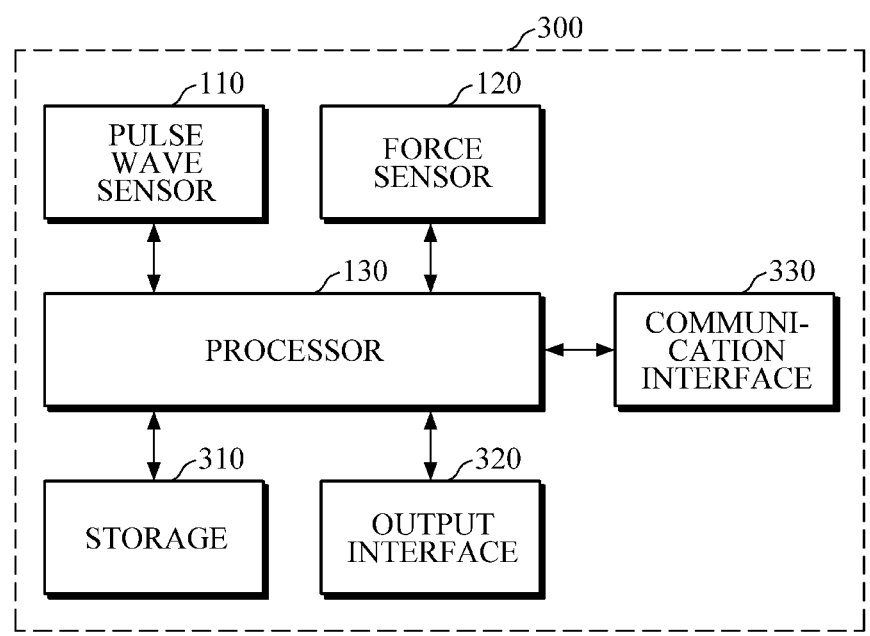
FIG. 3 is a block diagram illustrating an apparatus for estimating bio-information according to another embodiment of the present disclosure.

FIG. 3 is a block diagram illustrating an apparatus for estimating bio-information according to another embodiment of the present disclosure.

Referring to FIG. 3, an apparatus 300 for estimating bio-information includes the pulse wave sensor 110, the force sensor 120, the processor 130, a storage 310, an output interface 320, and a communication interface 230. The pulse wave sensor 110, the force sensor 120, and the processor 130 are described in detail above, such that the following description will be focused on non-overlapping parts.

The storage 310 may store information related to estimating bio-information. For example, the storage 310 may store data, such as the pulse wave signal, contact force, estimated bio-information value, feature vector, additional feature, and the like, which are processed by the pulse wave sensor 110, the force sensor 120, and the processor 130. In addition, the storage 310 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like, but is not limited thereto.

The output interface 320 may provide processing results of the processor 130 for a user. For example, the output interface 320 may display an estimated bio-information value on a display. In this case, if the estimated blood pressure value falls outside a preset normal range, the output interface 320 may provide a user with warning information by changing color, line thickness, etc., or displaying the estimated (abnormal) blood pressure value along with the preset normal range, so that the user may easily recognize the abnormal blood pressure value. Further, the output interface 320 may output information associated with bio-information in a non-visual manner by voice, vibrations, tactile sensation, and the like using a sound output module such as a speaker, or a haptic module and the like.

The communication interface 330 may communicate with an external device to transmit and receive various data, related to estimating bio-information, to and from the external device. In this case, the external device may include an information processing device such as a smartphone, a tablet PC, a desktop computer, a laptop computer, and the like. The communication interface 330 may communicate with the external device by using various wired or wireless communication techniques, such as Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, 5G communication, and the like. However, this is merely exemplary and is not intended to be limiting.

Figure 4:
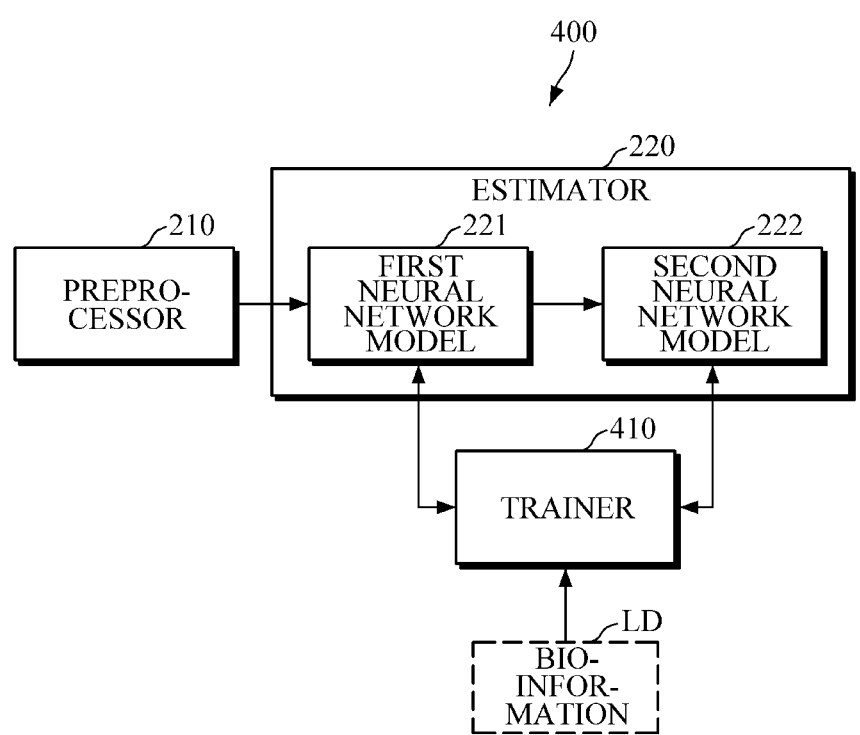
FIG. 4 is a block diagram illustrating an example of a configuration of a processor according to the embodiment of FIG. 3.

FIG. 4 is a block diagram illustrating an example of a processor 130 according to the embodiment of FIG. 3.

Referring to FIG. 4, a processor 400 according to an embodiment of the present disclosure includes the preprocessor 210, the estimator 220, and a trainer 410. The preprocessor 210 and the estimator 220 are described in detail above with reference to FIGS. 2A and 2B, such that a description thereof will be omitted.

The trainer 410 collects training data LD, and may train the first neural network model 221 and the second neural network model 222 by using the collected training data LD. The training data LD may include input features for each of the first neural network model 221, and the second neural network model 222, and ground-truth bio-information (e.g., a first ground truth blood pressure value and a second ground truth blood pressure value to be obtained from the first neural network model 221 and the second neural network model 222, respectively, based on the input features). The trainer 410 may receive estimated bio-information (e.g., a first estimated blood pressure value and a second estimated pressure value) from the first neural network model 221 and the second neural network model 222, respectively. The trainer 410 may apply a loss function to calculate a difference between the first ground truth blood pressure value and the first estimated blood pressure value as a first loss value, and calculate a difference between the second ground truth blood pressure value and the second estimated blood pressure value as a second loss value. The first loss value may be back propagated through the first neural network model 221, and the second loss value may be propagated through the second neural network model 222 and the first neural network model 221, to minimize the first loss value and the second loss value.

The trainer 410 may control the pulse wave sensor 110 and the force sensor 120 to acquire the pulse wave signal and force signal from a specific user or a plurality of users, and may collect the acquired signals as the training data LD. Further, the trainer 410 may output an interface on a display for a user to enter user characteristic information, reference blood pressure, and the like, and may collect data, input by the user through the interface, as the training data. In addition, the trainer 410 may control the communication interface 330 to receive pulse wave signals, force signals, and/or reference blood pressure values of users from an external device, such as a smartphone, a wearable device, a cuff manometer, and the like.

The trainer 410 may obtain a first reference input value, a second reference input value, and a third reference input value by using a plurality of reference pulse wave signals and reference force signals, and may train the first neural network model 221 by using the reference input values as input data of the first neural network model 221 and using reference pressure corresponding thereto as ground truth data. In this case, the first neural network model 221 is trained to output a feature vector associated with blood pressure in a previous layer of the last fully connected layer (2213 of FIGS. 2A and 2B). The feature vector output from the trained first neural network model 221 may be a feature having a high correlation with blood pressure. The trainer 310 may train the second neural network model 222 by using the feature vector, output from the first neural network model 221, and/or the additional feature as input data of the second neural network model 222, and using the reference blood pressure as ground truth data.

The trainer 410 may determine a time to train the neural network models 221 and 222 according to an operator's input or at predetermined intervals, or by analyzing a blood pressure estimation result, and the trainer 410 may train the neural network models 221 and 222 at a time when it is determined that training is required.

Further, the trainer 410 may transmit, through the communication interface 330, the trained neural network models 221 and 222 to an external device which estimates blood pressure by using the neural network models 221 and 222.

In this embodiment, accuracy may be improved by training a hybrid neural network model which is composed of the first neural network model 221 outputting the feature vector, and the second neural network model 222 outputting an estimated blood pressure value by using the feature vector, and by estimating blood pressure using the hybrid neural network model, as described above.

Figure 5:
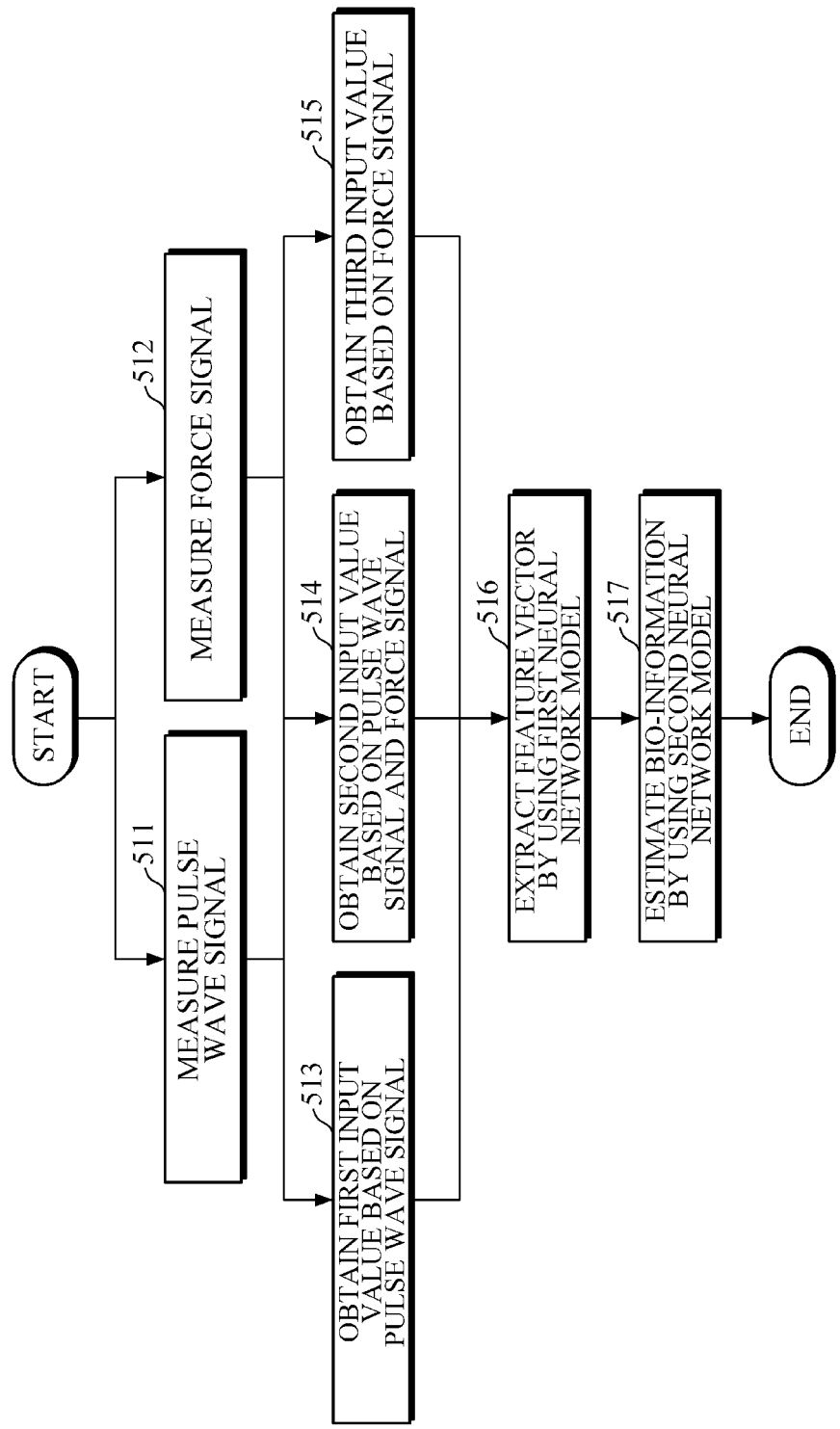
FIG. 5 is a flowchart illustrating a method of estimating bio-information according to an embodiment of the present disclosure.

FIG. 5 is a flowchart illustrating a method of estimating bio-information according to an embodiment of the present disclosure.

The method of FIG. 5 is an example of a method of estimating bio-information performed by the apparatuses 100 and 300 for estimating bio-information, which is described above in detail, and thus will be briefly described below.

First, when an object comes into contact with the pulse wave sensor, the apparatuses 100 and 300 for estimating bio-information may measure a pulse wave signal from the object by using the pulse wave sensor in operation 511, and may obtain a force signal by measuring an external force exerted onto the force sensor by using the force sensor in operation 512. The force sensor may be disposed below the pulse wave sensor, so that the external force exerted onto a contact surface of the pulse wave sensor is transferred to the force sensor that is located underneath the pulse wave sensor.

Then, the apparatuses 100 and 300 for estimating bio-information may obtain a first input value based on the pulse wave signal in 513. For example, the apparatuses 100 and 300 for estimating bio-information may obtain the pulse wave signal, a first order differential signal and/or a second order differential signal as the first input values. In this case, the apparatuses 100 and 300 for estimating bio-information may determine a waveform over the entire interval or a predetermined partial interval of the signals to be the first input value.

Further, the apparatuses 100 and 300 for estimating bio-information may obtain a second input value based on the pulse wave signal and the force signal in operation 514. For example, the apparatuses 100 and 300 for estimating bio-information may obtain an envelope of the pulse wave signal, an envelope of the first order differential signal and/an envelope of the second order differential signal by using the pulse wave signal, the first order differential signal and/or the second order differential signal, and the force signal. The apparatuses 100 and 300 and may obtain the envelope of the pulse wave signal, the envelope of the first order differential signal and/or the envelope of the second order differential signal as the second input values.

In addition, the apparatuses 100 and 300 for estimating bio-information may obtain a third input value based on the force signal in operation 515. For example, the apparatuses 100 and 300 for estimating bio-information may obtain, as the third input value, a force signal over the entire interval or a force signal over a predetermined interval from a predetermined time point, e.g., a time point corresponding to a maximum amplitude point in the envelope of the pulse wave signal.

Then, the apparatuses 100 and 300 for estimating bio-information may obtain a feature vector by inputting the first input value, the second input value, and the third input value into the first neural network model in operation 516. In particular, the first neural network model, into which the first input value, the second input value, and the third input value are input in parallel, may be trained to output a feature vector associated with blood pressure.

Subsequently, the apparatuses 100 and 300 for estimating bio-information may output an estimated bio-information value by inputting the feature vector, output in operation 516 from the first neural network model, into the second neural network model in operation 517.

Figure 6:
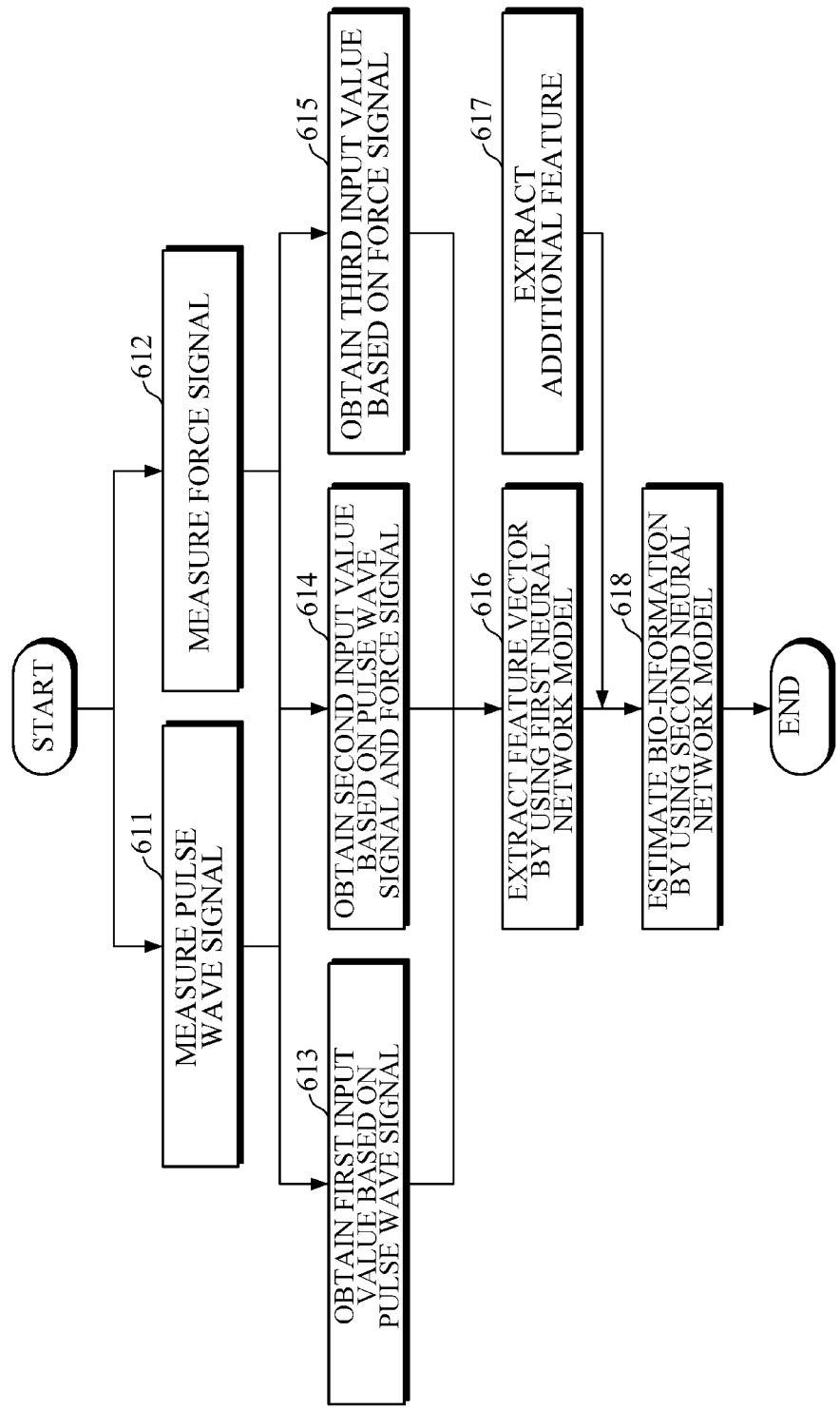
FIG. 6 is a flowchart illustrating a method of estimating bio-information according to another embodiment of the present disclosure.

FIG. 6 is a flowchart illustrating a method of estimating bio-information according to another embodiment of the present disclosure.

The method of FIG. 6 is an example of a method of estimating bio-information performed by the apparatuses 100 and 300 for estimating bio-information, which is described above in detail, and thus will be briefly described below.

First, when an object comes into contact with the pulse wave sensor, the apparatuses 100 and 300 for estimating bio-information may measure a pulse wave signal and a force signal from the object in operations 611 and 612.

Then, based on the pulse wave signal and/or the force signal, the apparatuses 100 and 300 for estimating bio-information may obtain a first input value, a second input value, and a third input value in operations 613, 614, and 615.

Subsequently, the apparatuses 100 and 300 for estimating bio-information may extract a feature vector by inputting the first input value, the second input value, and the third input value into the first neural network model in operation 616.

In addition, the apparatuses 100 and 300 for estimating bio-information may extract an additional feature in operation 617 based on user characteristic information, and/or the pulse wave signal and/or the force signal acquired in operations 611 and 612. For example, the additional feature HF may include user characteristic information, such as the user's age, gender, stature, and/or weight that is input from a user; and may include, for example, amplitude/time values at a maximum amplitude point of each signal, amplitude/time values at a local minimum point/local maximum point of each signal, a total/partial area of each signal waveform, a contact force value corresponding to a maximum amplitude point, a contact force value having a predetermined ratio to the contact pressure value at the maximum amplitude point, or a value obtained by properly combining the information, which are extracted by using the pulse wave signal, the first order differential signal, the second order differential signal, and/or the force signal.

Lastly, the apparatuses 100 and 300 for estimating bio-information may output an estimated bio-information value in operation 618 by inputting the feature vector and the additional feature, obtained in operations 616 and 617, into the second neural network model.

Figure 7:
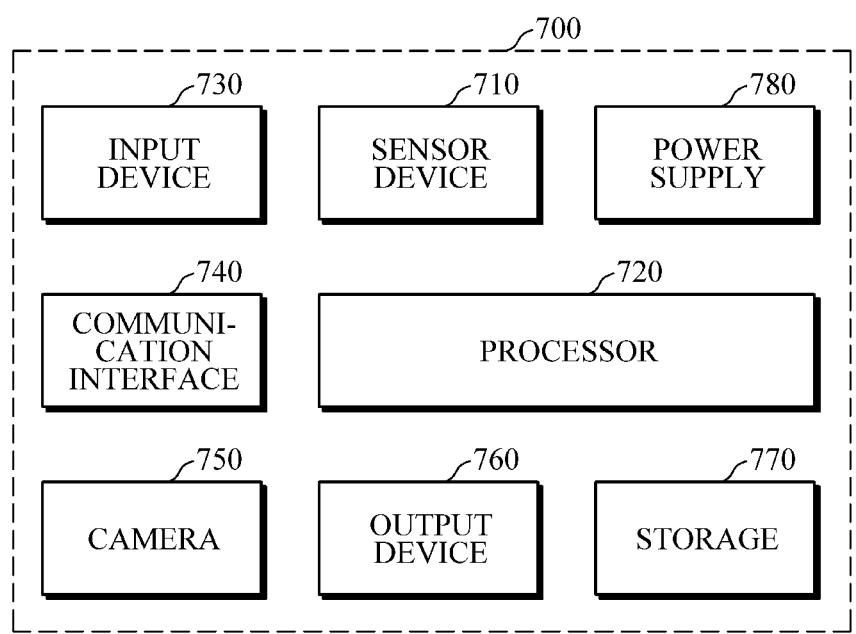
FIG. 7 is a block diagram illustrating an example of an electronic device including an apparatus for estimating bio-information.

FIG. 7 is a block diagram illustrating an electronic device including the apparatuses 100 and 300 for estimating bio-information.

In this example embodiment, the electronic device may include, for example, a wearable device of various types, e.g., a smart watch, a smart band, smart glasses, smart earphones, a smart ring, a smart patch, and a smart necklace, and a mobile device such as a smartphone, a tablet PC, etc., or home appliances or various Internet of Things (IoT) devices (e.g., home IoT device, etc.) based on Internet of Things (IoT) technology.

Referring to FIG. 7, the electronic device 700 may include a sensor device 710, a processor 720, an input device 730, a communication interface 740, a camera 750, an output device 760, a storage 770, and a power supply 780. All the components of the electronic device 700 may be integrally mounted in a specific device or may be distributed in two or more devices.

The sensor device 710 may include the pulse wave sensor and the force sensor of the aforementioned apparatuses 100 and 300 for estimating bio-information. The pulse wave sensor may include one or more light sources and detectors, and when an object comes into contact with the pulse wave sensor, the pulse wave sensor may acquire a pulse wave signal from the object. The force sensor may be disposed on an upper end or a lower end of the pulse wave sensor, and may measure a contact force exerted between the object and the pulse wave sensor. The sensor device 710 may include sensors for performing various other functions, for example, a gyro sensor, a Global Positioning System (GPS), and the like.

The processor 720 may execute programs, stored in the storage 770, to control components connected to the processor 720, and may perform various data processing or computation. The processor 720 may include a main processor, e.g., a central processing unit (CPU) or an application processor (AP), etc., and an auxiliary processor, e.g., a graphics processing unit (GPU), an image signal processor (ISP), a sensor hub processor, or a communication processor (CP), etc., which is operable independently from, or in conjunction with, the main processor.

In response to a user's request for estimating bio-information, the processor 720 may transmit a control signal to the sensor device 710, and may estimate bio-information by using the pulse wave signal and the force signal received from the sensor device 710. The processor 720 may train a hybrid neural network model for estimating bio-information, and may transmit the trained model to an external device through the communication model 740.

The input device 730 may receive a command and/or data to be used by each component of the electronic device 700, from a user and the like. The input device 730 may include, for example, a microphone, a mouse, a keyboard, or a digital pen (e.g., a stylus pen, etc.).

The communication interface 740 may support establishment of a direct (e.g., wired) communication channel and/or a wireless communication channel between the electronic device 700 and other electronic device, a server, or the sensor device 710 within a network environment, and performing of communication via the established communication channel. The communication interface 740 may include one or more communication processors that are operable independently from the processor 720 and supports a direct communication and/or a wireless communication. The communication interface 720 may include a wireless communication module, e.g., a cellular communication module, a short-range wireless communication module, or a global navigation satellite system (GNSS) communication module, etc., and/or a wired communication module, e.g., a local area network (LAN) communication module, a power line communication (PLC) module, and the like. These various types of communication modules may be integrated into a single chip, or may be separately implemented as multiple chips. The wireless communication module may identify and authenticate the electronic device 700 in a communication network by using subscriber information (e.g., international mobile subscriber identity (IMSI), etc.) stored in a subscriber identification module.

The camera 750 may capture still images or moving images. The camera 750 may include a lens assembly having one or more lenses, image sensors, image signal processors, and/or flashes. The lens assembly included in the camera 750 may collect light emanating from a subject to be imaged.

The output device 760 may visually/non-visually output data generated or processed by the electronic device 700. The output device 760 may include a sound output device, a display device, an audio module, and/or a haptic module.

The sound output device may output sound signals to the outside of the electronic device 700. The sound output device may include a speaker and/or a receiver. The speaker may be used for general purposes, such as playing multimedia or playing record, and the receiver may be used for incoming calls. The receiver may be implemented separately from, or as part of, the speaker.

The display device may visually provide information to the outside of the electronic device 700. The display device may include, for example, a display, a hologram device, or a projector and control circuitry to control the devices. The display device may include touch circuitry adapted to detect a touch, and/or sensor circuitry (e.g., pressure sensor, etc.) adapted to measure the intensity of force incurred by the touch.

The audio module may convert a sound into an electrical signal or vice versa. The audio module may obtain the sound via the input device, or may output the sound via the sound output device, and/or a speaker and/or a headphone of another electronic device directly or wirelessly connected to the electronic device 700.

The haptic module may convert an electrical signal into a mechanical stimulus (e.g., vibration, motion, etc.) or electrical stimulus which may be recognized by a user by tactile sensation or kinesthetic sensation. The haptic module may include, for example, a motor, a piezoelectric element, and/or an electric stimulator.

The storage 770 may store driving conditions required for driving the sensor device 710, and various data required for other components of the electronic device 700. The various data may include, for example, software and input data and/or output data for a command related thereto. The storage 770 may include a volatile memory and/or a non-volatile memory.

The power supply 780 may manage power supplied to the electronic device 700. The power supply 780 may be implemented as least part of, for example, a power management integrated circuit (PMIC). The power supply 780 may include a battery, which may include a primary cell which is not rechargeable, a secondary cell which is rechargeable, and/or a fuel cell.

Figure 8:
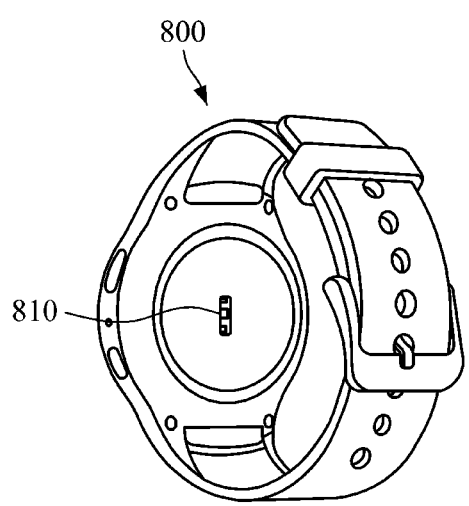
FIG. 8 is a diagram illustrating a wristwatch wearable device as an example of the electronic device of FIG. 7.
Figure 9:
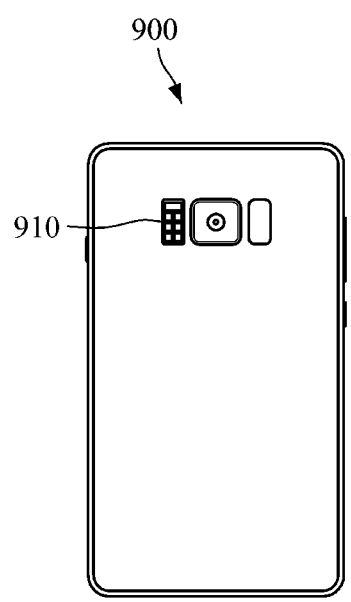
FIG. 9 is a diagram illustrating a mobile device as an example of the electronic device of FIG. 7.

FIGS. 8 and 9 are diagrams illustrating examples of structures of the electronic device of FIG. 7.

Referring to FIG. 8, the electronic device 700 may be implemented as a wristwatch wearable device 800, and may include a main body and a wrist strap. A display is provided on a front surface of the main body, and may display various application screens, including time information, received message information, and the like. A sensor device 810 may be disposed on a rear surface of the main body to measure a pulse wave signal and a force signal for estimating bio-information.

Referring to FIG. 9, the electronic device 700 may be implemented as a mobile device 900 such as a smartphone.

The mobile device 900 may include a housing and a display panel. The housing may form an exterior of the mobile device 900. The housing has a first surface, on which a display panel and a cover glass may be disposed sequentially, and the display panel may be exposed to the outside through the cover glass. A sensor device 910, a camera and/or an infrared sensor, and the like may be disposed on a second surface of the housing. When a user transmits a request for estimating bio-information by executing an application and the like installed in the mobile device 900, the mobile device 900 may estimate bio-information by using the sensor device 910, and may provide the estimated bio-information value as images and/or sounds to a user.

Figure 10:
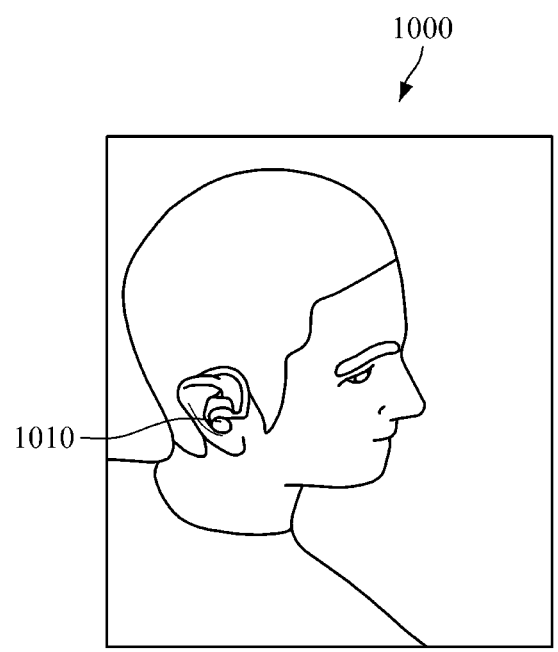
FIG. 10 is a diagram illustrating an ear-wearable device as an example of the electronic device of FIG. 7.

Referring to FIG. 10, the electronic device 700 may be implemented as an ear-wearable device 1000.

The ear-wearable device 1000 may include a main body and an ear strap. A user may wear the ear-wearable device 1000 by hanging the ear strap on a user's auricle. The ear strap may be omitted depending on the type of ear-wearable device 1000. The main body may be inserted into the external auditory meatus. A sensor device 1010 may be mounted in the main body. The ear-wearable device 1000 may provide a component estimation result as sounds to a user, or may transmit the estimation result to an external device, e.g., a mobile device, a tablet PC, a personal computer, etc., through a communication module provided in the main body.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating first bio-information and second bio-information, the apparatus comprising:
   a pulse wave sensor comprising a light source and a detector and configured to measure a pulse wave signal from an object;
   a force sensor comprising a strain gauge and configured to obtain a force signal by measuring an external force exerted onto the force sensor; and
   a processor configured to:
      obtain a first input value, a second input value, and a third input value based on the pulse wave signal and the force signal;
      extract a feature vector by inputting the first input value, the second input value, and the third input value into a first neural network model; and
      obtain the first bio-information by inputting the feature vector into a second neural network model,
   wherein the bio-information comprises one or more of blood pressure, vascular age, arterial stiffness, aortic pressure waveform, vascular compliance, stress index, fatigue level, skin age, skin elasticity,
   wherein the first neural network model comprises:
      three neural networks into which the first input value, the second input value, and the third input value are input respectively, and
      a first fully connected layer configured to output the feature vector by using outputs of the three neural networks as inputs; and
      a second fully connected layer configured to output the second bio information based on the feature vector output by the first fully connected layer, and
   wherein the second neural network model comprises:
      a third fully connected layer using the feature vector as an input; and
      a fourth fully connected layer outputting the first bio-information by using an output of the first fully connected layer as an input.

2. The apparatus of claim 1, wherein the first neural network model and the second neural network model are based on at least one of a Deep Neural Network, a Convolution Neural Network (CNN), and a Recurrent Neural Network (RNN).

3. The apparatus of claim 1, wherein three neural networks are arranged in parallel.

4. The apparatus of claim 3, wherein each of the three neural networks comprises:
   a first block comprising a first convolution layer, a first batch normalization layer, a first activation function layer, and a first pooling layer; and
   a second block comprising a second convolution layer, a second batch normalization layer, a second activation function layer, a third convolution layer, a third batch normalization layer, a skip connection path, and a third activation function.

5. The apparatus of claim 1, wherein the second neural network model further comprises a fifth fully connected layer using, as an input, an additional feature extracted based on at least one of user characteristic information, the pulse wave signal, and the force signal, and
   wherein an output of the fifth fully connected layer is input into the second fully connected layer.

6. The apparatus of claim 1, wherein the processor is further configured to obtain a first order differential signal and a second order differential signal from the pulse wave signal, and obtain at least one of the pulse wave signal, the first order differential signal, and the second order differential signal as the first input value.

7. The apparatus of claim 6, wherein by using the force signal, the processor is further configured to obtain at least one envelope of an envelope of the pulse wave signal, an envelope of the first order differential signal, and an envelope of the second order differential signal, and the at least one envelope as the second input value.

8. The apparatus of claim 7, wherein the processor is further configured to obtain the force signal as the third input value.

9. The apparatus of claim 8, wherein the processor is further configured to obtain, as the third input value, the force signal by measuring the force during a predetermined time period, starting from a reference point in time that corresponds to a maximum amplitude point in the envelope of the pulse wave signal.

10. The apparatus of claim 1, wherein the processor is further configured to preprocess the pulse wave signal and the force signal by using at least one of a band pass filter and a low pass filter.

11. The apparatus of claim 1, wherein the processor is further configured to obtain an additional feature based on at least one of user characteristic information, the pulse wave signal, and the force signal, and obtain the bio-information by inputting the feature vector and the obtained additional feature into the second neural network model.

12. The apparatus of claim 1, wherein the first neural network model and the second neural network model are jointly trained, by using a plurality of reference pulse wave signals and a plurality of reference force signals corresponding to the plurality of reference pulse wave signals, as training data.

13. The apparatus of claim 12, wherein the first neural network model is trained by inputting to the first neural network model, a first reference input value, a second reference input value, and a third reference input value that are obtained based on the plurality of reference pulse wave signals and the plurality of reference force signals; and
wherein the second neural network model is trained by inputting, to the second neural network model, a reference feature vector that is output from the first neural network model.

14. An electronic device comprising a main body, the apparatus of claim 1 which is disposed in the main body, and a display device configured to output the bio-information.

15. The electronic device of claim 14, wherein the electronic device corresponds to a wristwatch wearable device, an ear-wearable device, or a mobile device.

16. A method of estimating bio-information by an electronic device, the method comprising:
measuring a pulse wave signal from an object;
obtaining a force signal by measuring force exerted onto the electronic device by the object;
obtaining a first input value based on the pulse wave signal;
obtaining a second input value based on the pulse wave signal and the force signal;
obtaining a third input value based on the force signal;
extracting a feature vector by inputting the first input value, the second input value, and the third input value into a first neural network model; and
obtaining the bio-information by inputting the feature vector into a second neural network model,
wherein the bio-information comprises one or more of blood pressure, vascular age, arterial stiffness, aortic pressure waveform, vascular compliance, stress index, fatigue level, skin age, skin elasticity,
wherein the first neural network model comprises:
three neural networks into which the first input value, the second input value, and the third input value are input respectively, and
a first fully connected layer configured to output the feature vector by using outputs of the three neural networks as inputs; and
a second fully connected layer configured to output the second bio information based on the feature vector output by the first fully connected layer, and
wherein the second neural network model comprises:
a third fully connected layer using the feature vector as an input; and
a fourth fully connected layer outputting the bio-information by using an output of the first fully connected layer as an input.

17. The method of claim 16, wherein
three neural networks are arranged in parallel.

18. The method of claim 17, wherein each of the three neural networks comprise:
a first block comprising a first convolution layer, a first batch normalization layer, a first activation function layer, and a first pooling layer; and
a second block comprising a second convolution layer, a second batch normalization layer, a second activation function layer, a third convolution layer, a third batch normalization layer, a skip connection path, and a third activation function layer.

19. The method of claim 16, wherein the second neural network model further comprises a fifth fully connected layer using, as an input, an additional feature extracted based on at least one of user characteristic information, the pulse wave signal, and the force signal, and
wherein an output of the fifth fully connected layer is input into the second fully connected layer.

20. The method of claim 16, wherein the obtaining of the first input value comprises:
generating a first order differential signal and a second order differential signal from the pulse wave signal; and
obtaining at least one of the pulse wave signal, the first order differential signal, and the second order differential signal as the first input value.

21. The method of claim 20, wherein the obtaining of the second input value comprises:
by using the force signal, generating at least one envelope of an envelope of the pulse wave signal, an envelope of the first order differential signal, and an envelope of the second order differential signal; and
obtaining the at least one envelope as the second input value.

22. The method of claim 21, wherein the obtaining of the third input value comprises obtaining the force signal as the third input value.

23. The method of claim 22, wherein the obtaining of the third input value comprises obtaining, as the third input value, the force signal by measuring the force during a predetermined time period, starting from a reference point in time that corresponds to a maximum amplitude point in the envelope of the pulse wave signal.

24. The method of claim 16, further comprising obtaining an additional feature based on at least one of user characteristic information, the pulse wave signal, and the force signal, and wherein the obtaining of the bio-information comprises inputting the feature vector and the obtained additional feature into the second neural network model to obtain the bio-information.

25. An electronic device comprising:
a memory configured to store computer-readable instructions;
a processor configured to execute the computer-readable instructions to:
  obtain a first input value based on a pulse wave signal of a user, a second input value based on a force signal that indicates an external force exerted onto the electronic device while the pulse wave signal is obtained from the user, and a third input value based on the pulse wave signal and the force signal;
  input the first input value, the second input value, and the third input value to a first neural network to obtain a feature vector by a first neural network;
  obtain an additional bio-information feature based on a user input; and
  input the feature vector and the additional bio-information feature to a second neural network to obtain bio-information,
wherein the bio-information comprises one or more of blood pressure, vascular age, arterial stiffness, aortic pressure waveform, vascular compliance, stress index, fatigue level, skin age, skin elasticity,
wherein the first neural network comprises:
  three neural networks into which the first input value, the second input value, and the third input value are input respectively, and
  a first fully connected layer configured to output the feature vector by using outputs of the three neural networks as inputs; and
  a second fully connected layer configured to output the additional bio-information based on the feature vector output by the first fully connected layer, and
wherein the second neural network comprises:
  a third fully connected layer using the feature vector as an input; and
  a fourth fully connected layer outputting the bio-information by using an output of the first fully connected layer as an input.

* * * * *